United States Patent
Decker et al.

(10) Patent No.: US 7,182,789 B2
(45) Date of Patent: Feb. 27, 2007

(54) STABILISED COMPOSITIONS CONTAINING POLYFUNCTIONAL AZIRIDINE COMPOUNDS AS HARDENING CONSTITUENTS

(75) Inventors: Juergen Decker, Trier (DE); Stefan Adams, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/537,483

(22) PCT Filed: Nov. 28, 2003

(86) PCT No.: PCT/EP03/13424

§ 371 (c)(1), (2), (4) Date: Jun. 3, 2005

(87) PCT Pub. No.: WO2004/050617

PCT Pub. Date: Jun. 17, 2004

(65) Prior Publication Data

US 2006/0010609 A1    Jan. 19, 2006

(30) Foreign Application Priority Data

Dec. 3, 2002   (DE) ............................... 102 56 494

(51) Int. Cl.
*C14C 11/00*   (2006.01)

(52) U.S. Cl. ................. 8/94.1 R; 8/445; 106/287.3; 106/287.35

(58) Field of Classification Search ............... 8/445, 8/94.1, 94.1 R; 524/802; 106/287.35, 287.3
See application file for complete search history.

(56) References Cited

U.S. PATENT DOCUMENTS

| 3,671,256 A | | 6/1972 | Minsk |
| 4,025,503 A | * | 5/1977 | Miksovsky et al. ......... 548/964 |
| 4,960,687 A | | 10/1990 | Cho |
| 4,973,709 A | * | 11/1990 | Olson et al. ................ 548/954 |
| 6,436,540 B1 | * | 8/2002 | Garcia et al. ............ 428/423.1 |
| 6,465,566 B2 | * | 10/2002 | Garcia et al. ............... 524/591 |
| 2003/0208033 A1 | | 11/2003 | Venham et al. |

FOREIGN PATENT DOCUMENTS

| JP | 51 009434 | | 1/1976 |
| JP | 59 221321 | | 12/1984 |
| WO | 02/062894 | * | 8/2002 |

* cited by examiner

*Primary Examiner*—Lorna M. Douyon
*Assistant Examiner*—Amina Khan
(74) *Attorney, Agent, or Firm*—Oblon, Spivak, McClelland, Maier & Neustadt, P.C.

(57) ABSTRACT

The present invention relates to a composition comprising at least one polyfunctional aziridine compound and 1,4-diazabicyclo[2.2.2]octane. The present invention furthermore relates to the use of this composition as a curing component for formulations in the area of leather treatment, of coatings, of textile printing and of surface coatings.

7 Claims, No Drawings

STABILISED COMPOSITIONS CONTAINING POLYFUNCTIONAL AZIRIDINE COMPOUNDS AS HARDENING CONSTITUENTS

The present invention relates to a composition which contains at least one polyfunctional aziridine compound and 1,4-diazabicyclo[2.2.2]octane, and a process for its preparation. The present invention furthermore relates to the use of this composition as a curing component. The present invention also relates to the use of 1,4-diazabicyclo[2.2.2]octane for stabilizing aziridine-containing compounds and compositions.

Aziridine compounds have long been known and are widely used as curing components, for example for formulations in the area of leather treatment. Owing to their ring strain, aziridines are reactive compounds which react with a large number of reagents with ring opening. A disadvantage of this high reactivity of the aziridine unit is the limited storability of the aziridine compounds, since the products react with themselves and may thicken. Such thickening reduces the efficiency of aziridine compounds as curing components, since, on the one hand, the number of active aziridine units decreases and, on the other hand, the solubility and the dilutability of the curing component decline. In the extreme case, thickening leads to a completely insoluble and hence unusable curing product. The prior art describes different processes for stabilizing aziridine compounds.

U.S. Pat. No. 3,671,256 describes the use of aziridine units in the side chain of polymer curing agents, the aziridine units being stabilized by dilution in suitable, unreactive solvents.

U.S. Pat. No. 4,960,687 describes a process for the preparation of a substrate layer for a photographic film. In this process, inter alia, an aziridine-containing compound is used as a curing component. Owing to the low stability of this aziridine compound, it has to be stabilized by establishing a pH of from 9.0 to 11.5 in an aqueous system.

The disadvantage of these methods of stabilizing aziridine compounds is that, when using aziridine-containing compounds, the user is tied either to a specific solvent or to the use of aqueous solutions having a specific pH. In particular, the use of aqueous solutions of aziridine-containing compositions can lead to difficulties since some aziridine-containing compounds have only a limited stability in the presence of water.

It is an object of the present invention to provide a nonaqueous aziridine-containing composition in which the aziridine unit is stabilized without the disadvantages under discussion. It is furthermore intended to provide a process for the preparation of this aziridine-containing composition.

We have found that this object is achieved and that, according to the invention, 1,4-diazabicyclo[2.2.2]octane has a stabilizing effect on polyfunctional aziridine compounds.

The present invention therefore relates to a composition which contains at least one polyfunctional aziridine compound and 1,4-diazabicyclo[2.2.2]octane.

1,4-Diazabicyclo[2.2.2]octane (I), referred to as DABCO, is a bicyclic triethylenediamine which can be prepared by heating N-hydroxyethylpiperazine and is mainly used as a catalyst in polyurethane foaming and in esterifications.

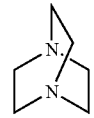

(I)

The novel composition contains at least one polyfunctional aziridine compound having at least two structural units of the formula (II),

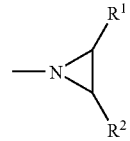

(II)

where $R^1$ and $R^2$, independently of one another, are each a hydrogen atom or an unfunctionalized or functionalized alkyl, alkenyl, aryl or aralkyl radical.

The content of 1,4-diazabicyclo[2.2.2]octane in the novel composition is preferably from 0.1 to 10, in particular from 0.3 to 5, preferably from 0.5 to 2.5, % by weight, based in each case on the composition.

The polyfunctional aziridine compound which is contained in the novel composition can preferably be chosen from the group consisting of the Michael adducts of unsubstituted or substituted ethylenimine with esters of polyhydric alcohols with α,β-unsaturated carboxylic acids and the adducts of unsubstituted or substituted ethylenimine with polyisocyanates.

Suitable alcohol components are, for example, trimethylolpropane, neopentylglycol, glycerol, pentaerythritol, 4,4'-isopropylidenediphenol and 4,4'-methylenediphenol. Suitable α,β-unsaturated carboxylic acids are, for example, acrylic and methacrylic acid, crotonic acid and cinnamic acid.

Particularly preferably, the novel composition contains acrylic esters.

The corresponding polyhydric alcohols of the α,β-unsaturated carboxylic esters can, if required, be alcohols which have been partly or completely extended with alkylene oxides at one or more of their OH functions. They may be, for example, the abovementioned alcohols extended at one or more OH functions with alkylene oxides. In this context, reference is also made to U.S. Pat. No. 4,605,698, the disclosure of which is hereby incorporated by reference into the present invention. Alkylene oxides particularly suitable according to the invention are ethylene oxide and propylene oxide.

Examples of aziridines suitable according to the invention are trimethylolpropane tris(beta-aziridino)propionate, neopentylglycol di(beta-aziridino)propionate, glyceryl tris(beta-aziridino)propionate, pentaerythrityl tetra(beta-aziridino)propionate, 4,4'-isopropylidenediphenol di(beta-aziridino)propionate, 4,4'-methylenediphenol di(beta-aziridino)propionate, 1,6-hexamethylenedi(N,N-ethyleneurea), 4,4'-methylenebis(phenyl-N,N-ethyleneurea), 1,3,5-tris(ω-hexamethylene-N,N-ethyleneurea)biuret and mixtures thereof.

The polyfunctional aziridine compounds can, if required, be substituted on their aziridine units.

The novel composition may additionally comprise a solvent which preferably has one or more of the following features: unreactive, organic, miscible with aqueous media, polar, nontoxic and economical. Polar, unreactive solvents, for example diacetone alcohol or N-methylpyrrolidone, are particularly suitable according to the invention. The content of solvent in the novel composition is preferably from 1 to 50, particularly preferably from 2 to 40, in particular from 3 to 30, especially from 4 to 20, % by weight, based in each case on the composition.

The present invention furthermore relates to a process for the preparation of the novel composition from a polyfunctional aziridine compound and 1,4-diazabicyclo[2.2.2]octane. For this purpose, a mixture of unsubstituted or substituted ethylenimine and 1,4-diazabicyclo[2.2.2]octane is provided, and at least one α,β-unsaturated carboxylic ester and/or at least one polyisocyanate are added.

The ester is preferably an alcohol polyesterified with α,β-unsaturated carboxylic acids. The alcohol is preferably selected from the group consisting of trimethylolpropane, neopentylglycol, glycerol, pentaerythritol, 4,4'-isopropylidenediphenol and 4,4'-methylenediphenol. Suitable α,β-unsaturated carboxylic acids are, for example, acrylic and methacrylic acid, crotonic and cinnamic acid.

Acrylic esters are particularly preferably used in the novel composition.

The alcohol can, if required, be partly or completely extended with alkylene oxide units at one or more of its OH functions. According to the invention, ethylene oxide and propylene oxide are particularly suitable for this purpose.

The polyisocyanate is preferably selected from the group consisting of hexamethylene diisocyanate, 4,4'-methylenebis(phenyl isocyanate) and 1,3,5-tris(ω-hexamethyleneisocyanato)biuret.

The present invention also relates to the compositions obtainable by this process.

The present invention furthermore relates to the use of the novel composition as a curing component for formulations in the area of leather treatment, of coatings, of textile printing and of surface coatings, it being possible to use the surface coatings in particular in road markings and paints. The novel compositions increase the water resistance of the surface coatings.

The present invention furthermore relates to the use of 1,4-diazabicyclo[2.2.2]octane for stabilizing aziridine-containing compounds and compositions. The present invention moreover relates to leather treatment compositions, coating compositions, textile printing compositions or surface coatings which contain the novel composition as a curing component. The surface coatings which contain the novel composition preferably serve for road marking or as paints.

The leather treatment compositions are preferably aqueous.

The amount of novel composition in the leather treatment compositions is preferably from 0 to 5, particularly preferably from 0.1 to 4, in particular from 0.2 to 3, especially from 0.3 to 2, % by weight, based in each case on the leather treatment composition.

The leather treatment compositions can, if required, comprise further additives customary for leather formulations. Examples of these are colored pigments, fillers, binders, bottoming compositions, (matt) seasoning agents, waxes, handle compositions, antifoams, leveling agents and dyes.

The amount of additives in these leather treatment compositions is preferably from 0 to 75, particularly preferably from 10 to 65, in particular from 20 to 60, especially from 25 to 55, % by weight, based in each case on the leather treatment composition.

The present invention has a number of advantages over the prior art.

According to the invention, the stabilization of the polyfunctional aziridine compounds is effected by 1,4-diazabicyclo[2.2.2]octane. The use of specific solvents or the establishing of a specific pH—which may be incompatible with specific applications of the polyfunctional aziridine compounds—is not necessary. The resulting novel compositions are storage-stable and light yellow and can be very readily processed. They are readily dilutable with water and have a relatively long processing time.

The examples which follow illustrate the present invention.

EXAMPLES

All amounts stated in the examples are in parts by weight.
a) Viscosity and Water Dilutability The novel formulations are prepared by reaction of ethylenimine and trimethylolpropane trisacrylate. 1,4-Diazabicyclo[2.2.2]octane is added to the ethylenimine before the synthesis of the aziridine compound. Only thereafter is the acrylate added.

The viscosity of the samples were measured according to Brookfield at 23° C. The water dilutability—homogeneity, processibility—was assessed by means of ratings.

The Following Formulations were Prepared

A1 (according to the invention): 90.2 parts of (III), 8.2 parts of N-methylpyrrolidone (NMP), 1.6 parts of 1,4-diazabicyclo[2.2.2]octane A2 (according to the invention): 90.2 parts of (III), 8.2 parts of diacetone alcohol, 1.6 parts of 1,4-diazabicyclo [2.2.2]octane B (comparative example): 100 parts of (III)

C (comparative example): 9.18 parts of (III), 8.2 parts of diacetone alcohol

D (comparative example): 98.4 parts of (III), 1.6 parts of 1,4-diazabicyclo[2.2.2]octane E (prior art): 99.0 parts of (III), 1.0 part of tetramethylethylenediamine (TMEDA) with

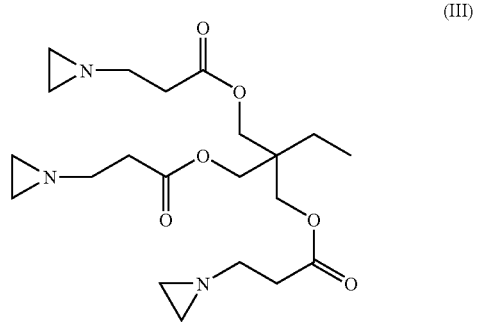

(III)

trimethylolpropane tris(beta-aziridino)propionate

| Storage time Sample | 4 weeks Viscosity [mPa · s]/ Water dilutability | 8 weeks Viscosity [mPa · s]/ Water dilutability | 12 weeks Viscosity [mPa · s]/ Water dilutability |
|---|---|---|---|
| A1, RT | 190/1 | 210/1 | 260/1 |
| A1, 50° C. | 320/1 | 420/1 | 500/2 |
| A2, RT | 260/1 | 270/1 | 270/1 |
| A2, 50° C. | 300/1 | 300/1 | 300/1 |
| B, RT | 580/3 | n.m. | n.m. |
| B, 50° C. | 1950/5 | n.m. | n.m. |

-continued

| Storage time Sample | 4 weeks Viscosity [mPa · s]/ Water dilutability | 8 weeks Viscosity [mPa · s]/ Water dilutability | 12 weeks Viscosity [mPa · s]/ Water dilutability |
|---|---|---|---|
| C, RT | 320/1 | 510/2 | 610/3 |
| C, 50° C. | 1360/4 | n.m. | n.m. |
| D, RT | 530/3 | 590/3 | 650/3 |
| D, 50° C. | 1020/4 | 1450/4 | 1620/4 |
| E, RT | 410/3 | 440/3 | 440/3 |
| R, 50° C. | 800/4 | 1480/4 | n.m. | n.m.: not measurable (sample thickens)

The novel compositions have a higher storage stability, a lower viscosity and better water dilutability.

b) Tendency to Yellowing

Polyfunctional aziridine compounds are used as components in formulations which are used in leather treatment or leather finishing. An undesired effect of the aziridine curing agents is the more pronounced yellowing of the leathers treated. The novel formulation with 1,4-diazabicyclo[2.2.2]octane shows substantially less tendency to yellowing compared with the prior art.

For the determination of the tendency to yellowing, a standardized surface (white-primed aluminum foil) was produced and this was then treated with a typical surface finishing formulation (top batch). After defined storage, the yellowness is measured.

Batch for Priming the Aluminum Foil:
Astacin Finish PF 400 parts
Lepton White N 100 parts
Demineralized water 200 parts,
spray until covered (15 g/DIN A4), then dry at 80° C.
Batch of Leather Treatment Formulations (Top Batch):

|  | 1 500 | 2 500 | 3 500 |
|---|---|---|---|
| Demineralized water | 460 | 450 | 450 |
| Thickener 6 | 40 | 40 | 40 |
| Sample E (prior art) |  | 10 |  |
| Sample A1 (according to the invention) |  |  | 10 |

Thickener 6=commercial polyurethane associative thickener, for example: 50:50 mixture of Collacral® PU85 and Solvenon® DPM.

Application to White-Primed Aluminum Foil
Amount applied: 20 g/m²
Tests: Storage at elevated temperatures and amount of yellowing using BCS-Win program The measurement is based on the Cielab calorimetric system, which is described in DIN 5033 (Sheet 1–9). The measurement is carried out in particular for the "Colorimetric determination of color differences in the case of body colors according to the CIELab formula" according to DIN 6174 with dE=total color difference and db=color difference in the direction of the yellow axis.

|  |  | 1 | 2 | 3 |
|---|---|---|---|---|
| 4h, 140° C. | dE | 0.42 | 0.42 | 0.24 |
|  | db | −0.09 | 0.34 | 0.1 |
| 6d, 100° C. | dE | 0.31 | 1.7 | 0.72 |
|  | db | 0.11 | 1.58 | 0.66 |

With the novel formulation A2, the yellowing at elevated temperature (dE total color change, db yellow component according to CIELab) can be reduced to values which are half as large as in the case of formulations of the prior art.

c) Crosslinker Activity

For the determination of crosslinker activity, the usual amounts of curing agent were added to conventional binder mixtures for leather treatment and leather pieces were finished and were tested with respect to curing, especially wet rub fastness:

Finishing on Undyed Side Leather

|  | Batches | | |
|---|---|---|---|
| Experiment number | 1a | 1b | |
| Water | 400 | 400 | |
| Sample E (prior art) | 6 |  | |
| Sample A1 (according to the invention) |  | 6 | |
| Lepton black N | 100 | 100 | Note: Pigment preparation comprising Carbon blank according to DE 41 42 240 |
| Corial microbinder AM | 300 | 300 | Note: Acrylate binder according to DE 33 44 354 |

Water and the "sample" were premixed in each case and added to a mixture of microbinder AM and Lepton black, then two crosses were sprayed wet (application with spray gun, corresponding to four-fold application (twice from top to bottom and twice from left to right)) (about 15 g/DIN A4), and drying was then effected 3 times in a drying channel. The samples were then plated for 3 seconds at 70° C./50 bar. This was followed by a second spray application with subsequent drying (without plating).

The samples were stored for 2 h at room temperature and then immediately tested with respect to wet rub fastness (limit=60 rubbing cycles without damage)

| Wet rub fastness 60×, damage | 0 | 0 |
|---|---|---|

Evaluation/damage: 0=none, s=slight, su=substantial, st=strong, vs=very strong The same performance is achieved with the novel formulation A1 as in the prior art (in spite of higher stabilizer content). The increased stabilizer content does not lead to a reduced or delayed effect.

The invention claimed is:

1. A composition consisting of at least one polyfunctional aziridine compound, 1,4-diazabicyclo[2.2.2]octane and a polar unreactive solvent.

2. The composition of claim 1, wherein the at least one polyfunctional aziridine compound has at least two structural units of the formula (II)

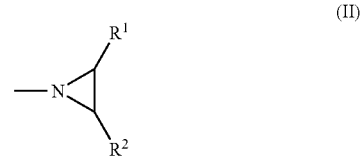

(II)

wherein R¹ and R², independently of one another, are each a hydrogen atom, a nonfunctionalized alkyl, alkenyl, aryl or aralkyl radical, or a functionalized alkyl, alkenyl, aryl or aralkyl radical.

3. The composition of claim 1, wherein the content of the 1,4-diazabicyclo[2.2.2]octane is from 0.1 to 10% by weight, based in each case on the composition.

4. The composition of claim 1, wherein the content of the solvent is from 1 to 50% by weight, based in each case on the composition.

5. The composition of claim 1, wherein the content of the 1,4-diazabicyclo[2.2.2]octane is from 0.1 to 10% by weight, based in each case on the composition, and wherein the content of the solvent is from 1 to 50% by weight, based in each case on the composition.

6. The composition of claim 1, wherein the at least one polyfunctional aziridine compound is selected from the group consisting of Michael adducts of substituted ethylenimine with α,β-unsaturated carboxylic esters of polyhydric alcohols, Michael adducts of unsubstituted ethylenimine with α,β-unsaturated carboxylic esters of polyhydric alcohols, adducts of substituted ethylenimine with polyisocyanates, and adducts of unsubstituted ethylenimine with polyisocyanates, or a combination thereof.

7. A composition as claimed in claim 2, wherein the polyfunctional aziridine compound is selected from the group consisting of the Michael adducts of substituted ethylenimine with α,β-unsaturated carboxylic esters of polyhydric alcohols, Michael adducts of unsubstituted ethylenimine with α,β-unsaturated carboxylic esters of polyhydric alcohols, the adducts of substituted ethylenimine with polyisocyanates, and the adducts of unsubstituted ethylenimine with polyisocyanates, or a combination thereof.

* * * * *